US007220768B2

(12) United States Patent
Bloom

(10) Patent No.: US 7,220,768 B2
(45) Date of Patent: May 22, 2007

(54) ISOXAZOLE-CONTAINING THIOUREA INHIBITORS USEFUL FOR TREATMENT OF VARICELLA ZOSTER VIRUS

(75) Inventor: Jonathan David Bloom, Nyack, NY (US)

(73) Assignee: Wyeth Holdings Corp., Madison, NJ (US)

( * ) Notice: Subject to any disclaimer, the term of this patent is extended or adjusted under 35 U.S.C. 154(b) by 524 days.

(21) Appl. No.: 10/772,799

(22) Filed: Feb. 5, 2004

(65) Prior Publication Data

US 2004/0157900 A1 Aug. 12, 2004

Related U.S. Application Data

(60) Provisional application No. 60/446,602, filed on Feb. 11, 2003.

(51) Int. Cl.
*A61K 61/42* (2006.01)

(52) U.S. Cl. ....................................... 514/378; 514/588

(58) Field of Classification Search ................ 514/588, 514/378

See application file for complete search history.

(56) References Cited

FOREIGN PATENT DOCUMENTS

WO WO 96/25157 * 8/1996
WO WO 97/40028 * 10/1997

* cited by examiner

*Primary Examiner*—Bruce R. Campell
*Assistant Examiner*—Emily M. Le
(74) *Attorney, Agent, or Firm*—Joseph M. Mazzarese

(57) ABSTRACT

This Invention provides a compound of the Formula:

wherein
X is or $R_1$, $R_2$, $R_3$ and $R_4$ are described in the specification and a pharmaceutical composition comprising the compound used for inhibiting replication of a herpes virus.

13 Claims, No Drawings

ISOXAZOLE-CONTAINING THIOUREA INHIBITORS USEFUL FOR TREATMENT OF VARICELLA ZOSTER VIRUS

BACKGROUND OF THE INVENTION

Eight viruses have been identified which are members of the family Herpesviridae (reviewed in Roizman, B. 1996. Herpesviridae, p. 2221–2230. In B. N. Fields, D. M. Knipe, and P. M. Howley (ed.), Fields Virology, 3rd ed. Lippincott-Raven Publishers, Philadelphia, Pa.). Each member of this family is characterized by an enveloped virus containing a proteinaceous segment and nucleocapsid, the latter of which houses the viruses' relatively large double-stranded DNA genome (i.e. approximately 80–250 kilobases). Members of the human alpha-herpes-virus subfamily are neurotropic and include herpes simplex virus type 1 (HSV-1) and type 2 (HSV-2), and varicella-zoster virus (VZV). The human beta-herpes-viruses are cytomegalovirus (HCMV), human herpesvirus 6 (HHV-6) and human herpesvirus 7 (HHV-7). The gamma-herpes-viruses are lymphotropic and include Epstein-Barr virus (EBV) and Kaposi's herpes-virus (HHV-8). Each of these herpes-viruses is causally related to human disease, including herpes labialis and herpes genitalis (HSV-1 and HSV-2), [Whitley, R. J. 1996, Herpes Simplex Viruses, p. 2297–2342, in B. N. Fields, D. M. Knipe, and P. M. Howley (ed.), Fields Virology, 3rd ed. Lippincott-Raven Publishers, Philadelphia, Pa.]; chicken pox and shingles VZV), [Arvin, A. 1996. Varicella-Zoster Virus, p. 2547–2585, In B. N. Fields, D. M. Knipe, and P. M. Howley (ed.), Fields Virology, 3rd ed, Lippincott-Raven Publishers, Philadelphia, Pa.]; infectious mononucleosis (EBV), [Rickinson, A. B. and Kieff, E. 1996, Epstein-Barr Virus, p. 2397–2446, In B. N. Fields, D. M. Knipe, and P. M. Howley (ed.), Fields Virology, 3rd ed, Lippincott-Raven Publishers, Philadelphia, Pa.]; pneumonia and retinitis (HCMV), [Britt, W. J., and Alford, C. A. 1996, Cytomegalovirus, p. 2493–2523, In B. N. Fields, D. M. Knipe, and P. M. Howley (ed.), Fields Virology, 3rd ed, Lippincott-Raven Publishers, Philadelphia, Pa.]; exanthem subitum (HHV-6), [Pellet, P. E, and Black, J. B. 1996, Human Herpes-virus 6, p. 2587–2608, In B. N. Fields, D. M. Knipe, and P. M. Howley (ed.), Fields Virology, 3rd ed. Lippincott-Raven Publishers, Philadelphia, Pa.] and (HHV-7), [Frenkel, N., and Roffman, E. 1996, Human Herpes-virus 7, p. 2609–2622, In B. N. Fields, D. M. Knipe, and P. M. Howley (ed.), Fields Virology, 3rd ed. Lippincott-Raven Publishers, Philadelphia, Pa.]; and Kaposi's sarcoma (HHV-8), [Neipel, F., Albrecht, J. C., and Fleckenstein, B. 1997, Cell-homologous genes in the Kaposi's sarcoma-associated rhadinovirus human herpes-virus 8: determinants of its pathogenicity? J. Virol. 71:4187–92, 1997]. HCMV is considered in more detail below. Following the primary infection, herpes-viruses establish latency within the infected individual and remain there for the remainder of his/her life. Periodic reactivation of latent virus is clinically relevant. In the case of HSV, reactivated virus can be transmitted to infants during birth, causing either skin or eye infection, central nervous system infection, or disseminated infection (i.e. multiple organs or systems). Shingles is the clinical manifestation of VZV reactivation. Treatment of HSV and VZV is generally with antiviral drugs such as acyclovir (Glaxo Wellcome), ganciclovir (Roche) and foscarnet (Asta) which target viral encoded DNA polymerase.

HCMV is a ubiquitous opportunistic pathogen infecting 50–90% of the adult population [Britt, W. J., and Alford, C. A. 1996, Cytomegalovirus, p. 2493–2523, In B. N. Fields, D. M. Knipe, and P. M. Howley (ed.), Fields Virology, 3rd ed. Lippincott-Raven Publishers, Philadelphia, Pa.]. Primary infection with HCMV is usually asymptomatic, although heterophile negative mononucleosis has been observed. The virus is horizontally transmitted by sexual contact, breast milk, and saliva. Intrauterine transmission of HCMV from the pregnant mother to the fetus occurs and is often the cause of serious clinical consequences. HCMV remains in a latent state within the infected person for the remainder of his/her life. Cell-mediated immunity plays a central role in controlling reactivation from latency. Impaired cellular immunity leads to reactivation of latent HCMV in seropositive persons.

HCMV disease is associated with deficient or immature cellular immunity. There are 3 major categories of persons with HCMV disease (reviewed by Britt and Alford, 1996). (1) In immunocompromised (AIDS) patients, HCMV is one of the two most common pathogens causing clinical disease (the other is *Pneumocystis*). The most common manifestation of HCMV in AIDS is retinitis, although infection of other organs including the adrenal glands, lungs, GI tract, and central nervous system are also reported frequently. 90% of AIDS patients have active HCMV infection; 25–40% (~85,000 patients in the United States) have life- or sight-threatening HCMV disease. HCMV is the cause of death in 10% of persons with AIDS. (2) Due to immune system suppression to reduce the risk of graft rejection, HCMV reactivation or reinfection is common amongst kidney, liver, heart, and allogeneic bone marrow transplant patients. Pneumonia is the most common HCMV disease in these patients, occurring in up to 70% of these transplant patients. (3) Congenital infection due to HCMV occurs in 1% of all births, about 40K per year. Up to 25% of these infants are symptomatic for HCMV disease between ages 0–3 years. HCMV disease is progressive, causing mental retardation and neurological abnormalities in children. Recent studies suggest that treatment with anti-HCMV drugs may reduce morbidity in these children.

Several antiviral drugs are currently being marketed [D. Bron, R. Snoeck, and L. Lagneaux 1996, New insights into the pathogenesis and treatment of cytomegalovirus, Exp. Opin. Invest. Drugs 5:337–344; Crumpacker, C. 1996, Ganciclovir, New Eng. J. Med. 335:721–729; Sachs, S., and F. Alrabiah, 1996, Novel herpes treatments: a review. Exp. Opin. Invest. Drugs 5:169–183]. These include: ganciclovir (Roche), a nucleoside analog with hemopoietic cell toxicity; foscarnet (Astra), a pyrophosphate analog with nephrotoxicity; and cidofovir; (Gilead), a nucleoside phosphonate with acute nephrotoxicity. Each of these drugs target the viral-encoded DNA polymerase, are typically administered intravenously due to their low bioavailability, and, as noted above, are the source of significant toxicity. Ganciclovir-resistant mutants which arise clinically are often cross-resistant with cidofovir. Hence, there is a need for safer (i.e. less toxic), orally bioavailable anti-viral drugs which are directed against novel viral targets.

Phenyl thioureas are disclosed for use in a variety of pharmaceutical applications. Armistead, et al., WO 97/40028, teaches phenyl ureas and thioureas as inhibitors of the inosine monophosphate dehydrogenase (IMPDH) enzyme which is thought to play a role in viral replication diseases such as herpes.

Widdowson, et al., WO 96/25157, teaches phenyl urea and thiourea compounds of the below formula for treating diseases mediated by the chemokine, interleukin-8.

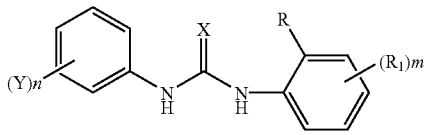

Morin, Jr., et al., U.S. Pat. No. 5,593,993 teaches certain phenyl thiourea compounds for treatment of AIDS and the inhibition of the replication of HIV and related viruses.

The compounds of this invention are potent structurally unique VZV inhibitors.

BRIEF SUMMARY OF THE INVENTION

This invention relates to compounds having the formula (I):

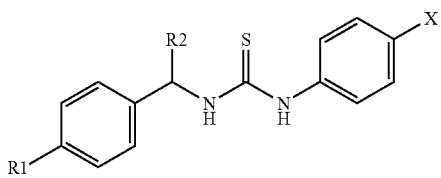

wherein
X is

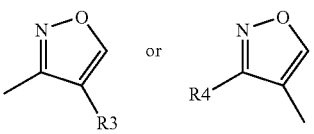

where $R_1$ is a halogen or hydrogen; $R_2$ is an alkyl group; $R_3$ is an alkyl group, cycloalkyl, hydroxymethyl, phenyl, substituted phenyl, benzyl or substituted benzyl group; $R_4$ is an alkyl group consisting of 1–6 carbon atoms, which may be further substituted with a substituted or unsubstituted phenyl, cycloalkyl, pyridyl, quinolinyl, 4-(1,2,3-thiadiazolyl), or imidazolyl group.

The preferred compounds of the present invention are the following compounds which include pharmaceutically acceptable salts thereof:

1-[1-(4-Fluorophenyl)-ethyl]-3-[4-(4-hydroxymethyl-isoxazol-3-yl)-phenyl]-thiourea;
1-[4-(4-Benzyl-isoxazol-3-yl)-phenyl]-3-[1-(4-fluorophenyl)-ethyl]-thiourea;
1-{4-[4-(4-Fluoro-benzyl)-isoxazol-3-yl]-phenyl}-3-[1-(4-fluorophenyl)-ethyl]-thiourea;
1-[1-(4-Fluorophenyl)-ethyl]-3-[4-(4-phenyl-isoxazol-3-yl)-phenyl]-thiourea;
1-[4-(4-tert-Butyl-isoxazol-3-yl)-phenyl]-3-[1-(4-fluorophenyl)-ethyl]-thiourea;
1-[1-(4-Fluorophenyl)-ethyl]-3-{4-[4-(2-fluorophenyl)-isoxazol-3-yl]-phenyl}-thiourea;
N-[1-(4-Fluorophenyl)ethyl]-N'-{4-[3-(3-pyridinyl)-4-isoxazolyl]phenyl}thiourea;
N-[1-(4-Fluorophenyl)ethyl]-N'-{4-[3-(4-quinolinyl)-4-isoxazolyl]phenyl}thiourea;
N-[1-(4-Fluorophenyl)ethyl]-N'-{4-[3-(4-pyridinyl)-4-isoxazolyl]phenyl}thiourea;
N-{4-[3-(4-Aminophenyl)-4-isoxazolyl]phenyl}-N'-[1-(4-fluorophenyl)ethyl]thiourea;
N-[1-(4-Fluorophenyl)ethyl]-N'-{4-[3-(1,2,3-thiadiazol-4-yl)-4-isoxazolyl]phenyl}thiourea;
N-[1-(4-Fluorophenyl)ethyl]-N'-{4-[3-(2-pyridinyl)-4-isoxazolyl]phenyl}thiourea;
N-(4-{3-[4-Dimethylamino)phenyl]-4-isoxazolyl}phenyl)-N'-[1-(4-fluorophenyl)ethyl]thiourea;
N-[1-(4-Fluorophenyl)ethyl]-N'-{4-[3-(4-hydroxyphenyl)-4-isoxazolyl]phenyl}thiourea;
N-[1-(4-Fluorophenyl)ethyl]-N'-[4-(3-phenyl-4-isoxazolyl)phenyl]thiourea;
N-[1-(4-Fluorophenyl)ethyl]-N'-{4-[3-(1H-imidazol-2-yl)-4-isoxazolyl]phenyl}thiourea; and
N-[1-(4-Fluorophenyl)ethyl]-N'-{4-[3-(2-hydroxyphenyl)-4-isoxazolyl]phenyl}thiourea.

In addition this invention relates to a pharmaceutical composition comprising a compound of formula (I) together with a pharmaceutical carrier.

In an embodiment this invention includes a method of inhibiting the replication of a herpes virus by contacting the virus with a compound of formula (I).

In another embodiment of this invention a patient suffering from a herpes virus infection is treated by administration of a therapeutically effective amount of a compound of formula (I)

DETAILED DESCRIPTION OF THE INVENTION

The novel compounds that comprise this invention are prepared according to Schemes I–III shown below.

Final compounds of the formula I are prepared by reacting isothiocyanates of formula II with aryl amines of the formula III in a suitable solvent at ambient temperature as outlined in Scheme I:

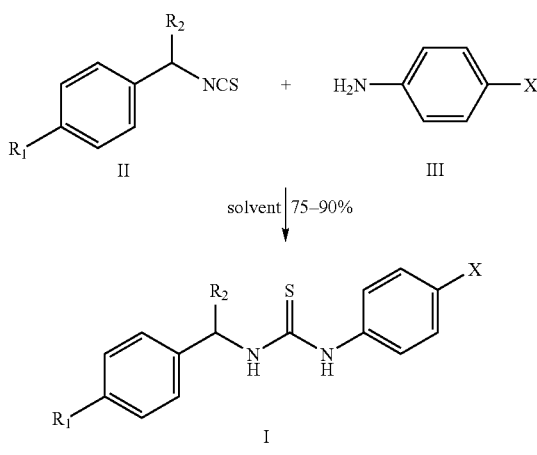

wherein X is

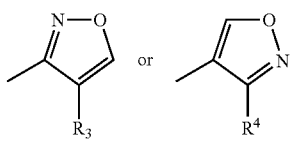

and $R_1$, $R_2$, $R_3$ and $R_4$ are as herein defined.

Unless otherwise defined, the terms used herein have the following meanings:

Alkyl as used herein refers to the radical of saturated aliphatic groups including straight or branched chain lower alkyl groups of 1 to 6 carbon atoms. The term "alkyl" is intended to include both "unsubstituted alkyls" and "substituted alkyls".

Cycloalkyl refers to a saturated mono or bicyclic ring system of 3 to 10 carbon atoms. Cycloalkyl groups of the present invention may be substituted or unsubstituted.

Phenyl as used herein refers to a 6 membered aromatic ring.

Halogen as used herein refers to chlorine, bromine, iodine and fluorine.

It will be understood that "substitution" or "substituted with" includes the implicit proviso that such substitution is in accordance with permitted valence of the substituted atom and the substituent, and that the substitution results in a stable compound. For purposes of this invention when a group is substituted a hydrogen on one or more carbons of the hydrocarbon backbone is replaced with any substituent that renders the molecule inactive against herpes. In a preferred embodiment substituents include a halogen, alkyl of 1 to 6 carbon atoms, cycloalkyl of 3 to 6 carbon atoms, heterocycloalkyl of 3 to 6 members, perfluoroalkyl of 1 to 6 carbon atoms, amino, azido, hydroxy, alkylamino, dialkylamino, aryl (including phenyl or substituted phenyl) or heteroaryl (including 5–10 membered mono- or bi-cyclic rings wherein heteroatom(s) is/are selected from O, S and N).

Carbon number refers to the number of carbons in the carbon backbone and does not include carbon atoms occurring in substituents such as an alkyl or alkoxy substituent.

Where terms are used in combination, the definition for each individual part of the combination applies unless defined otherwise. For instance, alkylcycloalkyl is an alkylcycloalkyl group in which alkyl and cycloalkyl are as previously described.

Pharmaceutically acceptable salts can be formed from a compound of the above general formula (I) and a pharmaceutically acceptable acid such as phosphoric acid, sulfuric acid, hydrochloric acid, hydrobromic acid, citric acid, maleic acid, succinic acid, fumaric acid, acetic acid, lactic acid, nitric acid, sulfonic acid, p-toluene sulfonic acid, methane sulfonic acid and the like.

The compounds of this invention contain a chiral center, providing for various steroisomeric forms of the compounds such as racemic mixtures as well as the individual optical isomers. In some preferred embodiments of the present invention the compounds of the present invention are substantially pure optical isomers. By substantially pure is meant the composition contains greater than 75% of the desired isomer and may include no more than 25% of the undesired isomer. In more preferred embodiments the pure optical isomer is greater than 90% of the desired isomer. In some preferred embodiments, when the target is VZV, the (S) isomer is preferred. The individual isomers can be prepared directly or by asymmetric or stereospecific synthesis or by conventional separation of optical isomers from the racemic mixture.

In another embodiment, the present invention provides a method for the prevention of replication of herpes virus infection including human cytomegalovirus, herpes simplex virus, and varicella zoster virus, thereby effectively treating a patient having a herpes virus infection. The present invention accordingly provides to a patient, a pharmaceutical composition that comprises a compound of this invention in combination or association with a pharmaceutically acceptable carrier. The compound of this invention may be administered alone or in combination with other therapeutically effective compounds or therapies for the treatment or prevention of herpes virus infection in a patient.

For purposes of this invention a patient is any mammal capable of becoming infected with an alpha or beta herpes virus as previously discussed. In a preferred embodiment a patient is a human.

The compounds are preferably provided orally or subcutaneously. The compounds may be provided by intralesional, intraperitoneal, intramuscular or intravenous injection; infusion; liposome-mediated delivery; topical, nasal, anal, vaginal, sublingual, urethral, transdermal, intrathecal, ocular or optic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 1000 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

For purposes of this invention a pharmaceutically acceptable carrier is a conventional excipient, such as a filler, a disintegrating agent, a binder, a lubricant, a flavoring agent, a color additive, suitable diluent, preservative, solubilizer, emulsifier, and/or, adjuvant. The carrier may be for example a diluent, an aerosol, a topical carrier, an aqueous solution, a nonaqueous solution or a solid carrier. The carrier may be a polymer or a toothpaste. A carrier in this invention also encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of herpes viral infection. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or preventing a herpes viral infection.

The compound of the present invention may be delivered locally via a capsule that allows a sustained release of the compound over a period of time. Controlled or sustained release compositions include formulation in lipophilic depots (for example, fatty acids, waxes, oils).

The present invention further provides a method of treating herpes virus infection in humans, which comprises administering to the infected individual an effective amount of a compound or a pharmaceutical composition of the invention.

An effective amount of the compound will vary with the severity of the disease and the physical condition of the patient and is determined by one of skill in the art.

Compounds of the present invention may be prepared by those skilled in the art of organic synthesis employing methods described below which utilize readily available reagents and starting materials unless otherwise described.

Regioisomeric isoxazoles of "X" are incorporated into compounds of formula III by the following methods: 3-Aryl substituted isoxazoles of formula III are prepared by converting suitable $R_4$-aldehydes of formula IV into their corresponding oximes which are then chlorinated (Scheme II). Chlorides of formula V are treated with a suitable base and reacted with 4-ethynylaniline at ambient temperature to afford isoxazoles of formula III.

Scheme II

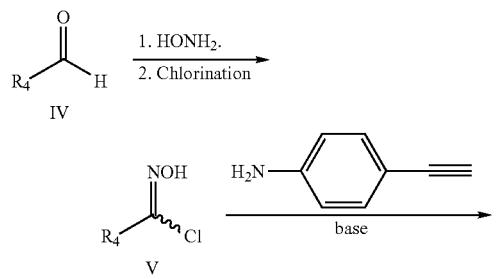

-continued

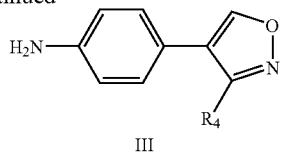

III

4-Aryl/aliphatic substituted isoxazoles are prepared according to Scheme III through a sequence that begins with amine protection of 4-amino benzyl alcohol. The benzylic alcohol is then oxidized to the corresponding aldehyde of formula VII using standard benzylic alcohol oxidation conditions. The resulting aldehyde is then reacted with hydroxylamine to give an oxime which is subsequently chlorinated to give a chloride of formula VIII.

The chloride of formula VIII is reacted with acetylenes of formula IX in the presence of base to afford cycloadducts of formula IX. Amine deprotection affords compounds of formula III which are used in Scheme I above.

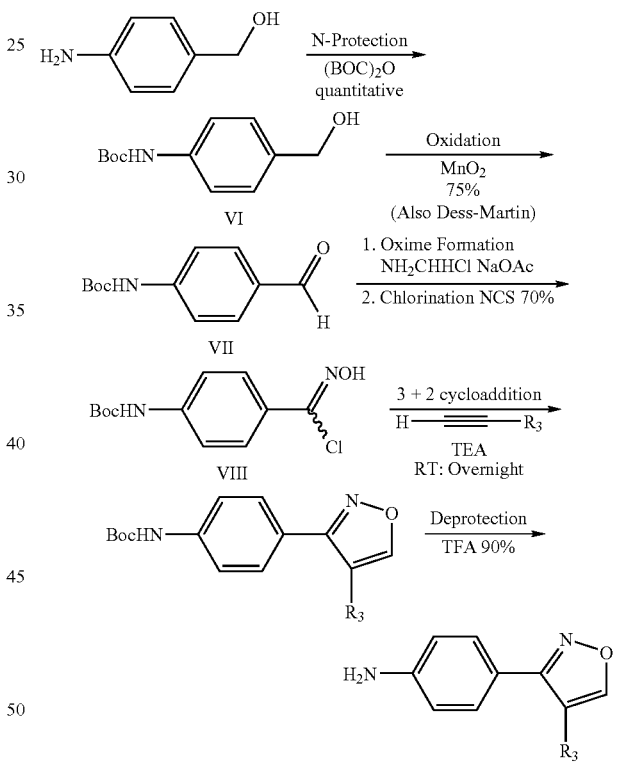

The following experimental details are set forth to aid in an understanding of the invention, and are not intended, and should not be construed, to limit in any way the invention set forth in the claims that follow thereafter.

EXAMPLE 1

(4-Hydroxymethylphenyl)carbamic acid tert-butyl ester

A solution of 4-aminobenzyl alcohol (1.0 g) in dioxane (5 mL)/water (5 mL)/1N sodium hydroxide (8 mL) at 0° C. is treated with di-tert-butyl dicarbonate (2.65 g) in one portion. The mixture is warmed up to room temperature and stirred for 6 hours at ambient temperature. Most of the dioxane is removed under reduced pressure. The aqueous concentrate is then extracted twice with ethyl acetate and the combined organic extract is washed with saturated aqueous sodium chloride, dried over anhydrous magnesium sulfate, concentrated under reduced pressure and pumped under high vacuum to give 1.8 g product as a white solid. MS: m/z 224 $(M+H)^+$.

EXAMPLE 2

(4-Formylphenyl)carbamic acid tert-butyl ester

Chromium trioxide (2.4 g) is added in portions to pyridine (29 mL) to maintain the temperature between 0°–10° C. A yellow suspension is formed. A solution of (4-hydroxymethylphenyl)carbamic acid tert-butyl ester (1.8 g) in pyridine (29 mL) is added dropwise to the yellow suspension. The reaction mixture is warmed to room temperature and stirred for 30 minutes. The reaction mixture is poured into water and extracted twice with ethyl acetate. The combined organics are washed with saturated aqueous sodium chloride, dried over anhydrous sodium sulfate, concentrated under reduced pressure and chromatographed on silica gel (4:1 ethyl acetate/hexane used as eluant) to give 1.09 g product as a white solid. MS: m/z 222 $(M+H)^+$.

EXAMPLE 3

[4-(Hydroxyiminomethyl)phenyl]carbamic acid tert-butyl ester

A solution of (4-formylphenyl)carbamic acid tert-butyl ester (1.0 g), hydroxylamine hydrochloride (0.31 g), and sodium acetate (0.37 g) in ethanol (8.5 mL)/water(1.5 mL) is heated at reflux temperature for 1 hour. The mixture is cooled to ambient temperature and partitioned between diethyl ether and water. The aqueous layer is back-extracted with diethyl ether and the combined organic extracts are washed with saturated sodium chloride, dried over anhydrous sodium sulfate and concentrated under reduced pressure to give 0.8 g pure white solid as the product. MS: m/z 237 $(M+H)^+$.

EXAMPLE 4

[4-(4-Benzylisoxazol-3-yl)phenyl]carbamic acid tert-butyl ester

A solution of [4-hydroxyiminomethyl)phenyl]carbamic acid tert-butyl ester (0.8 g) in dimethylformamide (8 mL) is treated with N-chlorosuccinimide (0.45 g) portionwise so as to maintain the temperature below 30° C. The reaction mixture is warmed to room temperature and partitioned between ethyl acetate and water. The organic layer is washed with saturated aqueous sodium chloride, dried over anhydrous sodium sulfate and concentrated under reduced pressure to give [4(hydroxyiminoylchloridemethyl)phenyl]carbamic acid tert-butyl ester. A solution of the latter (0.9 g) and 3-phenyl-1-propyne (0.26 g) in methylene chloride (9 mL) at 0° C. is treated with triethylamine (0.46 mL) dropwise. After addition, the mixture is warmed to room temperature and stirred for 12 hours. The reaction mixture is then concentrated under reduced pressure and chromatographed (ethyl acetate/hexane as eluant) on silica gel to give 0.362 g product as a white solid. MS: m/z 351 $(M+H)^+$.

EXAMPLE 5

4-(4-Benzylisoxazol-3-yl)phenylamine

Trifluoroacetic acid (0.5 mL) is added to [4-(4-benzylisoxazol-3-yl)phenyl]carbamic acid tert-butyl ester (0.3 g) and stirred for 30 minutes. The reaction mixture is concentrated under reduced pressure and the concentrate is partitioned between ethyl acetate and 1N sodium hydroxide solution. The organic layer is washed with saturated sodium chloride, dried over anhydrous magnesium sulfate and chromatographed on silica gel (ethyl acetate/hexane as eluant) to give 0.15 g product as a white solid. MS: m/z 251 $(M+H)^+$.

EXAMPLE 6

4-(Dimethylamino)benzaldehyde oxime

A solution of 4-(dimethylamino)benzaldehyde (5.0 g), hydroxylamine hydrochloride (2.3 g), and sodium acetate (2.7 g) in ethanol (61 mL)/water (11 mL) is heated at reflux temperature for 1 hour. The mixture is cooled to ambient temperature and partitioned between diethyl ether and water. The aqueous layer is back-extracted with diethyl ether and the combined organic extracts are washed with saturated sodium chloride, dried over anhydrous sodium sulfate and concentrated under reduced pressure to give 2.6 g pure white solid as the product. MS: m/z 165 $(M+H)^+$.

EXAMPLE 7

N-{4-[4-(4-Aminophenyl)-3-isoxazolyl]phenyl}-N,N-dimethylamine

A solution of 4-(dimethylamino)benzaldehyde oxime (2.6 g) in dimethylformamide (18 mL) is treated with N-chlorosuccinimide (2.1 g) portionwise so as to maintain the temperature below 30° C. The reaction mixture is warmed to ambient temperature and partitioned between ethyl acetate and water. The organic layer is washed with saturated aqueous sodium chloride, dried over anhydrous sodium sulfate and concentrated under reduced pressure to give 4-(dimethylamino)benzhydroximinoyl chloride. A solution of the later (2.9 g) and 4-ethynylaniline (0.85 g) in methylene chloride (46 mL) at 0° C. is treated with triethylamine (2.0 mL) dropwise. After addition, the mixture is warmed to room temperature and stirred for 12 hours. The reaction mixture is then concentrated under reduced pressure and chromatographed (ethyl acetate/hexane as eluant) on silica gel to give 0.21 g product as a white solid. MS: m/z 280 $(M+H)^+$.

EXAMPLE 8

1-[4-(4-benzylisoxazol-3-yl)phenyl]-3-[1-(4-fluorophenyl)ethyl]thiourea

A solution of 4-(4-benzyl-isoxazol-3-yl)-phenylamine and 4-fluoro-α-methyl-benzyl isothiocyanate in dimethylformamide (5 mL) is stirred for 12 hours at room temperature. The reaction mixture is then partitioned between ethyl acetate and water. The organic layer is washed with saturated aqueous sodium chloride, dried over anhydrous magnesium sulfate and concentrated under reduced pressure to give 1.4 g crude product as a yellow solid. The latter is recrystallized from ethyl acetate/hexane to give 0.9 g product as a yellow solid. MS: m/z 433 $(M+H)^+$.

TABLE 1 final compounds prepared as described in
example 8 with appropriate starting materials

| Example | Name | M + H |
|---|---|---|
| 9 | 1-[1-(4-Fluorophenyl)ethyl]-3-[4-(4-hydroxymethylisoxazol-3-yl)phenyl]thiourea | 372 |
| 10 | 1-[4-(4-Benzylisoxazol-3-yl)phenyl]-3-[1-(4-fluorophenyl)ethyl]thiourea | 433 |
| 11 | 1-{4-[4-(4-Fluorobenzyl)isoxazol-3-yl]phenyl}-3-[1-(4-fluorophenyl)ethyl]thiourea | 451 |
| 12 | 1-[1-(4-Fluoropheny)ethyl]-3-[4-(4-phenylisoxazol-3-yl)phenyl]thiourea | 419 |
| 13 | 1-[4-(4-tert-Butylisoxazol-3-yl)phenyl]-3-[1-(4-fluorophenyl)ethyl]thiourea | 399 |
| 14 | 1-[1-(4-Fluorophenyl)ethyl]-3-{4-[4-(2-fluorophenyl)isoxazol-3-yl]phenyl}thiourea | 437 |
| 15 | N-[1-(4-Fluorophenyl)ethyl]-N'-{4-[3-(3-pyridinyl)-4-isoxazolyl]phenyl}thiourea | 420 |
| 16 | N-[1-(4-Fluorophenyl)ethyl]-N'-{4-[3-(4-quinolinyl)-4-isoxazolyl]phenyl}thiourea | 470 |
| 17 | N-[1-(4-Fluorophenyl)ethyl]-N'-{4-[3-(4-pyridinyl)-4-isoxazolyl]phenyl}thiourea | 420 |
| 18 | N-{4-[3-(4-Aminophenyl)-4-isoxazolyl]phenyl}-N'-[1-(4-fluorophenyl)ethyl]thiourea | 434 |
| 19 | N-[1-(4-Fluorophenyl)ethyl]-N'-{4-[3-(1,2,3-thiadiazol-4-yl)-4-isoxazolyl]phenyl}thiourea | 427 |
| 20 | N-[1-(4-Fluorophenyl)ethyl]-N'-{4-[3-(2-pyridinyl)-4-isoxazolyl]phenyl}thiourea | 420 |
| 21 | N-(4-{3-[4-(Dimethylamino)phenyl]-4-isoxazolyl}phenyl)-N'-[1-(4-fluorophenyl)ethyl]thiourea | 462 |
| 22 | N-[1-(4-Fluorophenyl)ethyl]-N'-{4-[3-(4-hydroxyphenyl)-4-isoxazolyl]phenyl}thiourea | 435 |
| 23 | N-[1-(4-Fluorophenyl)ethyl]-N'-[4-(3-phenyl-4-isoxazolyl)phenyl]thiourea | 419 |
| 24 | N-[1-(4-Fluorophenyl)ethyl]-N'-{4-[3-(1 H-imidazol-2-yl)-4-isoxazolyl]phenyl}thiourea | 409 |
| 25 | N-[1-(4-Fluorophenyl)ethyl]-N'-{4-[3-(2-hydroxyphenyl)-4-isoxazolyl]phenyl}thiourea | 435 |

Human Cytomegalovirus

Yield Assay. Monolayer cultures of human foreskin fibroblasts are infected with HCMV wild-type virus, typically at a multiplicity of infection equal to 0.2, in the presence of inhibitors compound (varying concentrations). At three days post-infection, total virus produced in these cultures (i.e. virus yield) is assessed by harvesting and titering the virus in 12-well plates of cultured human foreskin fibroblasts (done in the absence of inhibitors). Plaques are quantified at 2 weeks post-infection. An inhibitor of HCMV is identified by the reduction in titer of virus yield in the presence, compared to the titer in the absence of compound. In this assay, the relative anti-HCMV activity of an inhibitor is typically determined by calculating the $IC_{50}$ or $IC_{90}$ value, that is, the amount of compound required to reduce the virus yield by 50% or 90%, respectively. Table 2 describes $IC_{50}$ data for compounds tested against HCMV.

Microtiter Plate Assay. Ninety-six well plate cultures of human foreskin fibroblasts are infected in the presence of inhibitor compound with a HCMV recombinant mutant virus whose genome contains the prokaryotic beta-glucuronidase gene (Jefferson, R. A., S. M. Burgess, and D. Hirsh. 1986. Beta-glucuronidase from *Escherichia coli* as a gene fusion marker. Proc. Natl. Acad. Sci. USA 83:8447–8451) whose expression is controlled by a viral promoter. An example of such a virus is RV145 [T. R. Jones; V. P. Muzithras, and Y. Gluzman. 1991, Replacement mutagenesis of the human cytomegalovirus genome: US10 and US11 gene products are nonessential, J. Virol. 65:5860–5872]. Since it is under the control of a viral promoter, beta-glucuronidase expression is an indirect indicator of growth and replication of HCMV in this assay. At 96 hours post-infection, the infected cell lysates are prepared (using 50 mM sodium phosphate [pH 7.0] containing 0.1% Triton X-100 and 0.1% sarkosyl) and assayed for beta-glucuronidase activity using a substrate for the enzyme which when cleaved yields either a product which can be measured colorimetrically in a spectrophotometer or fluorescently in a microfluorimeter. Examples of such substrates are p-nitrophenyl-beta-D-glucuronide and methylumbelliferylglucuronide, respectively. The presence of an antiviral compound is indicated by the reduced expression of the HCMV genome resident beta-glucuronidase gene, compared to the absence of inhibitor. Thus, the generation of the chromophore of fluorophore product in this assay is correspondingly reduced. Data from this assay generated using varying amounts of inhibitor compound is also used to estimate the $IC_{50}$ of an inhibitor compound.

HSV Antiviral (ELISA) Assay. Vero cells (ATCC #CCL-81) are plated on 96-well tissue culture plates at $3.5 \times 10^4$ cells per 100 µl tissue culture DMEM (Dulbecco's modified Eagle media) supplemented with 2% fetal bovine serum (FBS) in each well. After overnight incubation, inhibition was determined by comparing the fluorescence obtained in absence of compound to that obtained in the presence of compound.

The following compounds were tested for activity as herpes virus inhibitors.

TABLE 2

| | $IC_{50}$ values in µg/mL | | | | |
|---|---|---|---|---|---|
| EXAMPLE | VZV | MTS | CMV | HSV | RSV |
| 9 | 2 | >15 | 5.7 | >10 | 7.2 |
| 10 | 0.086 | >15 | 2.4 | >10 | >10 |
| 11 | 0.16 | 1.9 | 1.8 | 2.1 | 4.7 |
| 12 | 0.37 | >15 | >10 | >10 | >10 |
| 13 | 0.23 | 1.5 | 1.3 | 2.3 | 2.1 |
| 14 | 5.4 | >15 | >10 | >10 | >10 |
| 15 | 0.19 | 14.0 | >10 | 3.1 | >10 |
| 16 | 0.08 | 6.5 | 0.8 | 3.1 | 2.3 |
| 17 | 0.14 | 5.5 | 0.93 | 3.7 | 1.5 |
| 18 | 0.05 | 13 | 2.0 | >10 | >10 |
| 19 | 0.13 | >15 | 0.9 | >10 | >10 |
| 20 | 0.18 | >15 | >10 | >10 | >10 |
| 21 | 0.34 | >15 | 9.3 | >10 | >10 |
| 22 | 0.61 | >15 | 2.5 | >10 | 9.9 |
| 23 | 0.89 | >15 | >10 | >10 | >10 |
| 24 | 1.00 | >15 | >10 | >10 | >10 |
| 25 | 1.90 | >15 | 7.9 | >10 | >10 |

What is claimed:

1. A compound of formula (I):

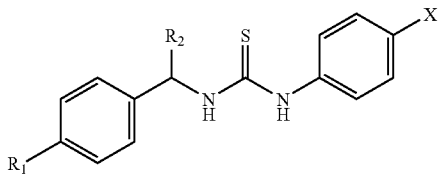

wherein
R₁ is a halogen or hydrogen;
R₂ is an alkyl group;
X is

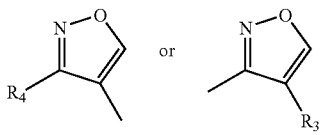

R₃ is an alkyl group, cycloalkyl, hydroxymethyl, phenyl, substituted phenyl, benzyl group, or substituted benzyl group; and
R₄ is an alkyl group, which may be further substituted with a substituted or unsubstituted phenyl, cycloalkyl, pyridyl, quinolinyl, 4-(1,2,3-thiadiazolyl), or imidazolyl group;
or a pharmaceutically acceptable salt thereof.

2. A compound as claimed in claim 1 wherein R₂ is methyl.

3. A compound as claimed in claim 1 wherein R₁ is fluorine.

4. A compound as claimed in claim 1 wherein R₃ is hydroxymethyl, phenyl, p-fluorophenyl, benzyl, p-fluorobenzyl or tert-butyl.

5. A compound as claimed in claim 1 wherein R₄ is phenyl, 2-hydroxyphenyl, 4-hydroxyphenyl, 4-aminophenyl, 4-dimethylaminophenyl, 3-pyridyl, 4-pyridyl, 4-quinolyl, 4-(1,2,3-thiadiazolyl) or imidazol-2-yl.

6. A compound of formula:

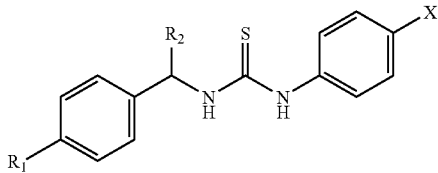

wherein
R₁ is hydrogen, F;
R₂ is an alkyl;
X is

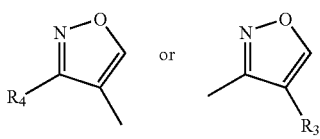

R₃ is an alkyl, cycloalkyl, hydroxymethyl, phenyl, substituted phenyl, benzyl or substituted benzyl group; and
R₄ is an alkyl group, which may be further substituted with a substituted or unsubstituted phenyl, cycloalkyl, pyridyl, quinolinyl, 4-(1,2,3-thiadiazolyl), or imidazolyl group;
or a pharmaceutically acceptable salt thereof.

7. A compound of claim 1 selected from:
N-{4-[3-(4-aminophenyl)-4-isoxazolyl]phenyl}-N'-[1-(4-fluorophenyl)ethyl]thiourea;
N-[1-(4-fluorophenyl)ethyl]-N'-{4-[3-(1,2,3,-thiadiazol-4-yl)-4-isoxazolyl]phenyl}thiourea;
N-[1-(4-fluorophenyl)ethyl]-N'-{4-[3-(2-pyridinyl)-4-isoxazolyl]phenyl}thiourea;
N-(4-{3-[4-(dimethylamino)phenyl]-4-isoxazolyl}phenyl)-N'-[1-(4-fluorophenyl)ethyl]thiourea;
1-[1-(4-Fluorophenyl)-ethyl]-3-[4-(4-hydroxymethyl-isoxazol-3-yl)-phenyl]-thiourea;
1-[4-(4-Benzyl-isoxazol-3-yl)-phenyl-3-[1-(4-fluorophenyl)-ethyl]-thiourea;
1-{4-[4-(4-Fluoro-benzyl)-isoxazol-3-yl]-phenyl}-3-[1-(4-fluorophenyl)-ethyl]-thiourea;
1-[1-(4-Fluorophenyl)-ethyl]-3-[4-(4-phenyl-isoxazol-3-yl)-phenyl]-thiourea;
1-[1-4-(4-tert-Butyl-isoxazol-3-yl)-phenyl]-3-[1-(4-fluorophenyl)-ethyl]-thiourea;
1-[1-(4-Fluorophenyl)-ethyl]-3-{4-[4-(2-fluorophenyl)-isoxazol-3-yl]-phenyl}-thiourea;
N-[1-(4-Fluorophenyl)ethyl]-N'-{4-[3-(3-pyridinyl)-4-isoxazolyl]phenyl}thiourea;
N-[1-(4-Fluorophenyl)ethyl-N'-{4-[3-(4-quinolinyl)-4-isoxazolyl]phenyl}thiourea;
N-[1-(4-Fluorophenyl)ethyl-N'-{4-[3-(4-pyridinyl)-4-isoxazolyl]phenyl}thiourea;
N-[1-(4-Fluorophenyl)ethyl]-N'-{4-[3-(4-hydroxyphenyl)-4-isoxazolyl]phenyl}thiourea;
N-[1-(4-Fluorophenyl)ethyl-N'-[4-(3-phenyl-4-isoxazolyl)phenyl]thiourea;
N-[1-(4-Fluorophenyl)ethyl]-N'-{4[-3-(1H-imidazol-2-yl)-4-isoxazolyl]phenyl}thiourea; and
N-[1-(4-Fluorophenyl)ethyl]-N'-{4-[3-(2-hydroxyphenyl)-4-isoxazolyl]phenyl}thiourea.

8. A composition comprising a compound of formula (I) as claimed in claim 1 or a pharmaceutically acceptable salt thereof, together with a pharmaceutical carrier.

9. A method of inhibiting the replication of a herpes virus comprising contacting a compound of formula (I) as claimed in claim 1 or a pharmaceutically acceptable salt thereo, with an alpha or beta herpes virus.

10. The method of claim 9 wherein the herpes virus is human cytomegalovirus.

11. The method of claim 9 where the herpes virus is herpes simplex virus.

12. The method of claim 9 where the herpes virus is varicella zoster virus.

13. A process for preparing a compound according to claim 1 which comprises reacting a compound of formula II:

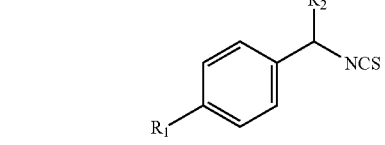

wherein R₁ and R₂ are as defined in claim 1, with a compound of formula III

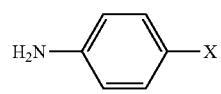

wherein X is a defined in claim 1, and if desired isolating the compound of formula I prepared as a pharmaceutically acceptable salt.

* * * * *